US00PP12769P2

(12) United States Plant Patent
Bak et al.

(10) Patent No.: US PP12,769 P2
(45) Date of Patent: Jul. 9, 2002

(54) GUZMANIA PLANT NAMED 'JAZZ'

(75) Inventors: Elly Bak, Rijsenhout; Nicolaas D. M. Steur, Oude Niedorp, both of (NL)

(73) Assignee: Corn. BAK B.V., Assendelft (NL)

( * ) Notice: Subject to any disclaimer, the term of this patent is extended or adjusted under 35 U.S.C. 154(b) by 0 days.

(21) Appl. No.: 09/451,865

(22) Filed: Dec. 1, 1999

(51) Int. Cl.[7] ..... A01H 5/00
(52) U.S. Cl. ..... Plt./371
(58) Field of Search ..... Plt./371

(56) References Cited

U.S. PATENT DOCUMENTS

PP10,575 P * 8/1998 Bak et al. ..... Plt./371

OTHER PUBLICATIONS

GTITM UPOVROM Citation for 'Jazz' as per QZ PBR 990754; May 20, 1999.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A Guzmania plant named 'Jazz' particularly characterized by its steady growth habit in a funnel-form rosette measuring approximately 42 cm in height above the pot when flowering; numerous, relatively narrow leaves, each approximately 3–3.5 cm in width and 30–42 cm in length; superior primary bract production; compound inflorescence; floral bracts are bright orange, which especially distinguishes the new cultivar from others known to the Inventors, including the cultivar 'Jive'; and long-lasting leaves and inflorescence color.

2 Drawing Sheets

BACKGROUND OF THE INVENTION

The present invention comprises a new and distinct cultivar of Guzmania that is an inter-specific hybrid, hereinafter referred to by the cultivar name 'Jazz'.

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Desirably, the plants are shaded from direct sunlight, and during the spring to autumn period, the central vase-like part of the leaf rosette is desirably filled with water.

Guzmania is native to tropical America. Leaves of Guzmania are usually formed as basal rosettes, which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots produced by the plant which may then be rooted. The resulting plantlets are detached from the mother plant and may be potted in a suitable growing mixture.

Methods for cultivaton and crossing of Guzmania are well known. For a detailed discussion, reference is made to the following publications, which are incorporated herein by reference: Benzing, David H., *The Biology of the Bromeliads*, Mad River Press, Inc., Eureka (1980); Zimmer, Karl,

*Bromelien*, Verlag Paul Parey, Berlin (1986); and Rauh, Werner, *Bromelien*, Verlag Eugen Ulmer, Stuttgart (1981).

The new cultivar 'Jazz' is a product of a planned breeding program and was originated by the inventors from a cross made during such a program in Assendelft, The Netherlands, in 1994. The male or pollen parent was a proprietary selection of *Guzmania lingulata minor* identified by Code No. 94206011. The female or seed parent was a proprietary selection of *Guzmania wittmackii* identified by Code No. 94206206.

The selection which is the variety 'Jazz' was chosen after commencement of flowering of the progeny of the cross of 94206011×94206206 in 1997 in Assendelft, The Netherlands. The selection was first asexually propagated through offshoots by, or under the supervison of, the inventors in Assendelft, with subsequent asexual reproduction through offshoots. Continuous asexual propagation has demonstrated that the combination of characteristics as herein disclosed for the new cultivar 'Jazz', as observed in Assendelft, The Netherlands, are firmly fixed and reproduces true to type through successive generations of asexual reproduction.

Both parents have a degree of homozygosity such that the progeny of the cross 94206011×94206206 are phenotypically uniform and identical to 'Jazz'. Accordingly, plants which are phenotypically identical to 'Jazz' can be produced by sexual reproduction as well as asexual reproduction.

'Jazz' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar. For example, substantial differences in plant height and diameter, and the number of leaves, can result depending on the size of the plant at the time flowering is induced by acetylene treatment. Since treatment with acetylene to induce flowering disrupts normal watering and fertilization regimens, acetylene treatment of relatively smaller plants adversely affects the growth of the plant.

The closest comparison cultivar is Guzmania 'Jive' (U.S. Plant Pat. No. 10,968). The most important difference is the color brightness of the inflorescence. The inflorescence of Guzmania 'Jazz' is brighter in color than the inflorescence of Guzmania 'Jive'.

In comparison to 'Jazz' which has a plant height of approximately 42 cm, the male parental cultivar is a small plant measuring approximately 20 cm in height, and the female parental cultivar is approximately 70 cm in height.

BRIEF DESCRIPTION OF THE INVENTION

'Jazz' is particulary characterized by the following characteristics:

1. Steady growth habit in a funnel-form rosette measuring approxiamately 42 cm in height above the pot when flowering;
2. Numerous, relatively narrow leaves, each approximately 3–3.5 cm in width and 30–42 cm in length;
3. Superior primary bract production;
4. Compound inflorescence;
5. Floral bracts are bright orange, which especially distinguishes the new cultivar from others known to the Inventors, including the cultivar 'Jive'; and
6. Long-lasting leaves and inflorescence color.

Guzmania 'Jazz' is a steady, long-lasting hybrid with superior bract-production and a compound and orange inflorescence that exhibits good keeping quality.

BRIEF DESCRIPTION OF THE DRAWINGS

The accompanying color photographs show typical inflorescence and foliage characteristics of 'Jazz', with colors being as true as possible with illustrations of this type.

Sheet 1 is a side view of a plant of 'Jazz' showing the primary and floral bracts.

Sheet 2 is a close-up view of the inforescence and floral bracts of 'Jazz'.

DETAILED BOTANICAL DESCRIPTION

The following traits have been repeatedly observed and in combination distinguish 'Jazz' as a new and distinct cultivar. These observations, measurements and descriptions were taken of 'Jazz' plants grown under greenhouse conditions which approximate those generally used in commercial practice. Plants described were about 10 to 12 months old after potting. In the following description, color references are made to The Royal Horticultural Society (R.H.S.) Colour Chart. The new cultivar flowers approximately 11 weeks after treatment with acetylene.

Plant:

*Form.*—Funnel-form rosette.
*Height.*—Approximately 42 cm high, when flowering.
*Growth habit.*—Stemless.
*Diameter.*—Approximately 50 cm.
*Crop time.*—Approximately 10 to 12 months after potting, a flowering plant is produced.

Foliage:

*Color.*—Upper surface: RHS 147A. Under surface: RHS 137A.
*Size of leaf.*—Length: Approximately 30–42 cm. Width: Approximately 3.0–3.5 cm.
*Shape of leaf.*—Linear-lanceolate.
*Surface texture.*—Smooth.
*Orientation.*—Leaf blades arch continuously from the base.
*Variegation.*—None.
*Apex.*—Acute.
*Margin.*—Entire.
*Number of leaves.*—Approximately 27.

Bracts:

*Scape bracts.*— Length: Lowest are approximately 30 cm long. The scape bracts just below the primary bracts are approximately 14 cm long. Width: Approximately 3.5 cm. General Shape: Lanceolate. Texture: Smooth. Margin: Entire. Apex: Acute. Color: RHS 44B (Both surfaces). Number: Approximately 10.
*Primary bracts.*—Length: Lowest are approximately 14 cm long. The bracts progress upwardly, they become shorter, with the top primary bracts approximately 6 cm in length. Width: Approximately 3 cm. General Shape: Ovate-lanceolate. Texture: Smooth. Margin: Entire. Apex: Acute. Color: Upper surface RHS 14B, lower surface RHS 44B; Number: Approximately 12.
*Top primary bracts.*—Apex: Acute. Color: RHS 14B (Both surfaces).

Flowers:

*Borne (stalks).*—Erect.
*Type of inflorescence.*—Compound.
*Shape.*—Panicle.
*Size of inflorescence on stalk.*—Approximately 15 cm high and approximately 20 cm in diameter.
*Individual petals.*—(Mostly disposed within the floral bracts hidden behind the primary bracts). Length: Approximately 6 cm. Width: Approximately 0.5 cm. Quantity: Approximately 75 flowers divided over approximately 11 branches depending on the size of the plant. Color: Yellow (RHS 14A) (Both surfaces).
*Time of blooming.*—A fully grown plant can bloom throughout the entire year starting approximately eleven (11) weeks after natural induction or through treatment with acetylene.
*Duration of blooms.*—Each flower blooms for a total of one (1) day and the total blooming time for the plant is approximately five (5) weeks.

Reproductive organs:

*Ovaries.*—Superior.
*Stamens.*—Six (6) in number.

*Seed characteristics:* Sterile hybrid, therefore, no seed or fruit produced.

Disease/pest resistance/susceptibility: No observations made to date.

We claim:

1. A new and distinct cultivar of Guzmania plant named 'Jazz', substantially as illustrated and described.

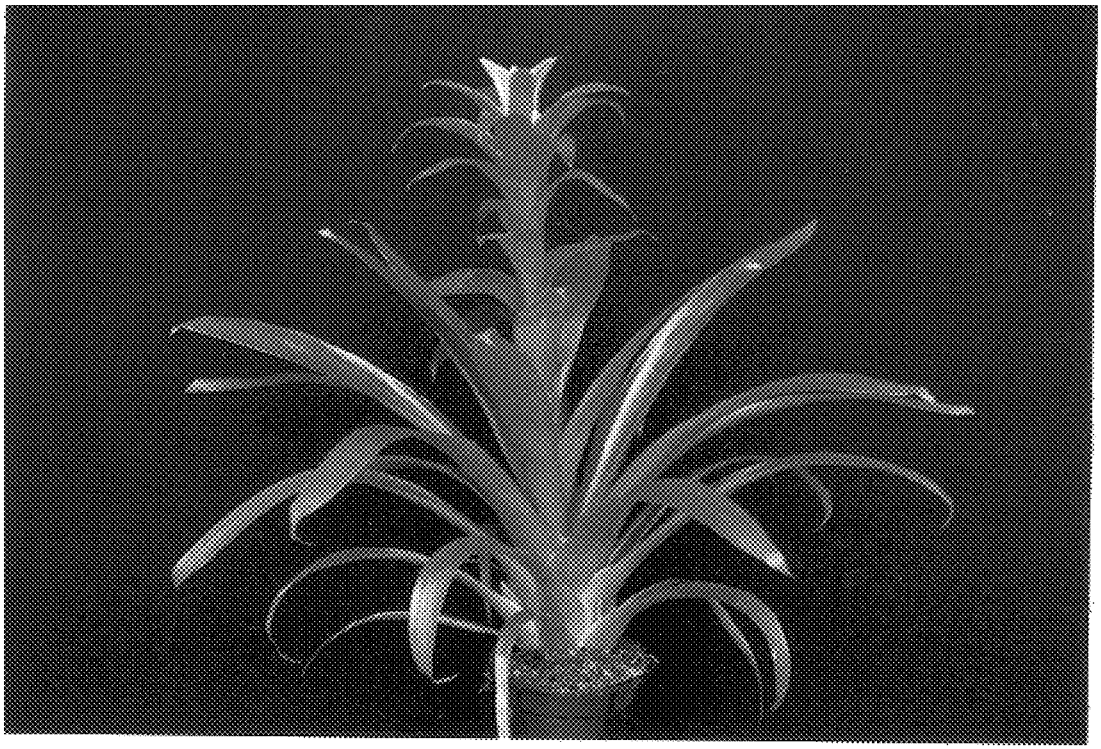

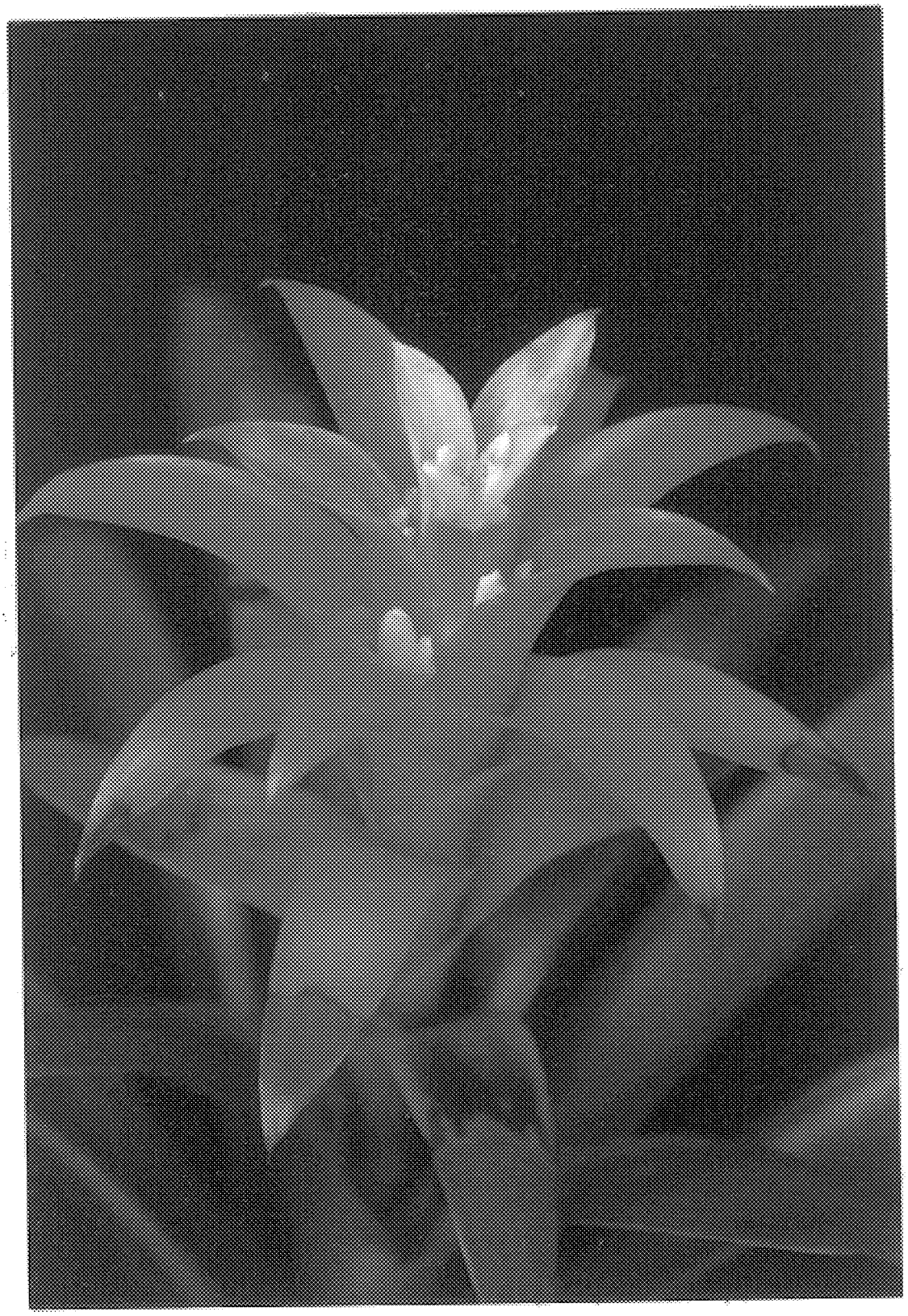

* * * * *